US00PP18036P3

(12) United States Plant Patent
Németh

(10) Patent No.: US PP18,036 P3
(45) Date of Patent: Sep. 18, 2007

(54) ***THUJA* PLANT NAMED 'SILVANUS 1'**

(50) Latin Name: *Thuja occidentalis*
Varietal Denomination: Silvanus 1

(76) Inventor: Jenö Németh, Petöházi u. 1., Fertöszentmiklós (HU), H-9444

( * ) Notice: Subject to any disclaimer, the term of this patent is extended or adjusted under 35 U.S.C. 154(b) by 78 days.

(21) Appl. No.: 11/231,188

(22) Filed: Sep. 20, 2005

(65) Prior Publication Data

US 2006/0064790 P1 Mar. 23, 2006

(30) Foreign Application Priority Data

Sep. 22, 2004 (HU) ..... F04 00057

(51) Int. Cl.
*A01H 7/00* (2006.01)

(52) U.S. Cl. ..... Plt./213

(58) Field of Classification Search ..... Plt./213
See application file for complete search history.

(56) References Cited

PUBLICATIONS

UPOV–ROM GTITM, Plant Variety Database, 2006/01 GTI Jouve Retrieval Software, Citation for Thuja 'Silvanus 1. Sz. Klon' one page.*

* cited by examiner

*Primary Examiner*—Kent Bell
*Assistant Examiner*—June Hwu
(74) *Attorney, Agent, or Firm*—The Webb Law Firm

(57) ABSTRACT

'Silvanus 1' is a new variety of *Thuja occidentalis* that exhibits medium dense branching and is suitable for use as a solitary garden plant or for use as a field hedge.

2 Drawing Sheets

Botanical classification: *Thuja occidentalis.*
Varietal denomination: 'Silvanus 1'.

CROSS REFERENCE TO RELATED APPLICATION

The present invention claims priority to Hungarian Plant Patent Application No. F04 00057, filed on Sep. 22, 2004.

BACKGROUND OF THE INVENTION

The present invention comprises a new and distinct cultivar of *Thuja occidentalis* known by the varietal name 'Silvanus 1'. The new variety was discovered by the breeder as a naturally-occurring branch (sport) mutation of *Thuja occidentalis* 'Smaragd' in West Hungary. 'Silvanus 1' was first asexually reproduced by semi-hardwood cuttings in West Hungary. The new variety has been trial and field tested and has been found to retain its distinctive characteristics and remain true to type through successive propagations. Table 1 illustrates characteristics that distinguish 'Silvanus 1' from its parent plant, 'Smaragd'.

TABLE 1

| Characteristic | 'Silvanus 1' | 'Smaragd' |
|---|---|---|
| Plant habit | Ovoid | Conic |
| Plant speed of growth | Slow | Medium |
| Color of upper leaf side in Summer | Light green | Green |
| Side branch position | Vertical | Horizontal |
| Scale leaf width | Narrow | Medium |
| Scale leaf thickness | Thin to medium | Medium |

DESCRIPTION OF THE DRAWINGS

The accompanying photographic drawings illustrate the new variety, with the color being as nearly true as is possible with color illustrations of this type.

DESCRIPTION OF THE PLANT

Figure 1:
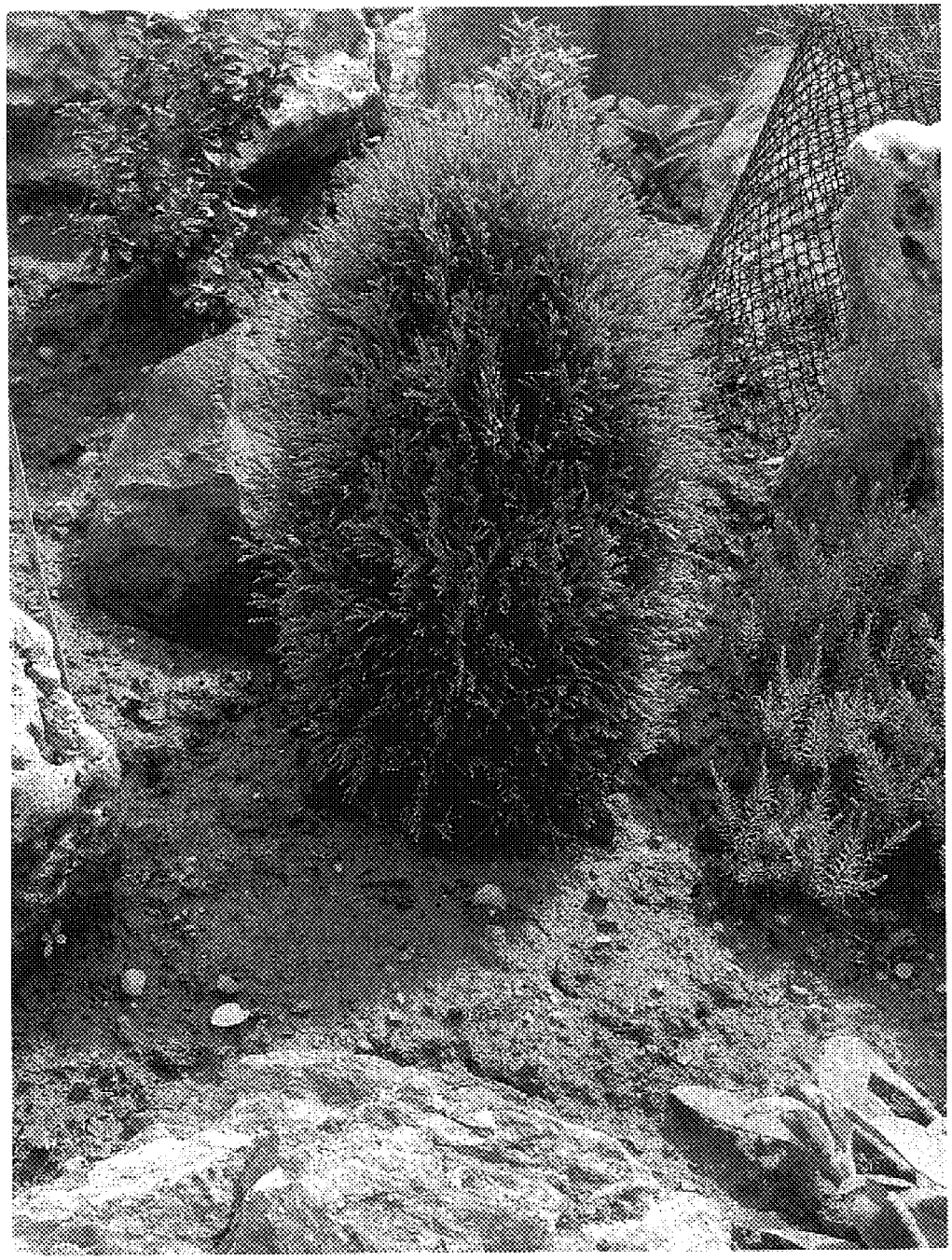
FIG. 1 shows an entire plant of the new variety.
Figure 2:
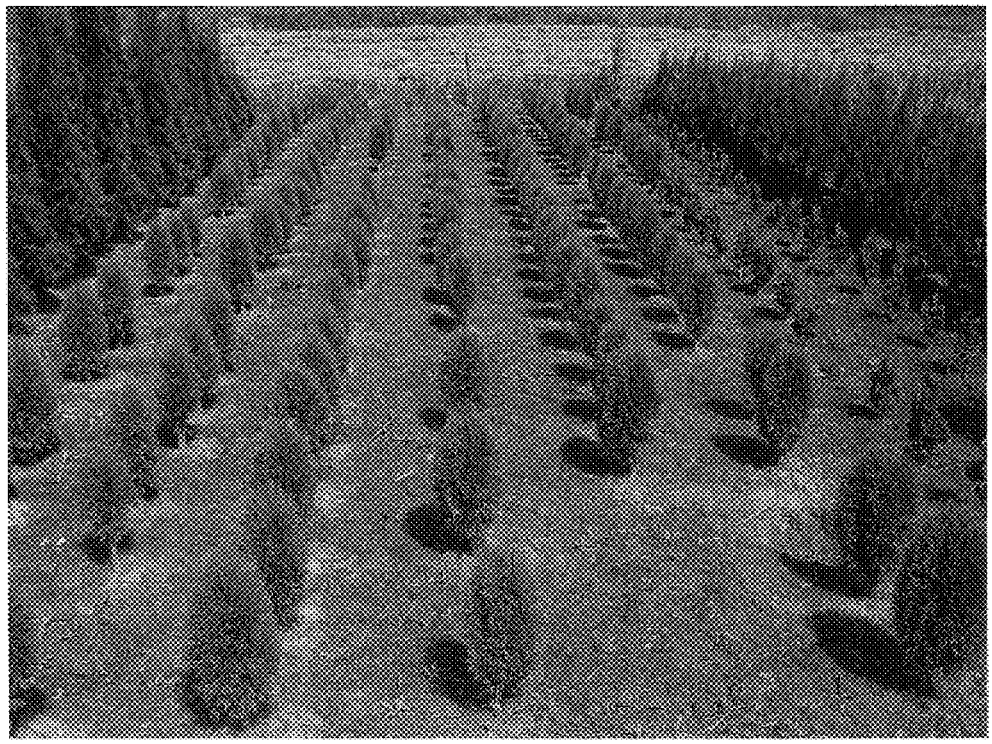
FIG. 2 shows an entire field of the new variety.

The following detailed description sets forth the characteristics of the new cultivar. The data which defines these characteristics were collected by asexual reproductions carried out in West Hungary. The new variety was grown outside without shade in average productivity soil after a Summer season that experienced more rain than average. 'Silvanus 1' was four years old when described and was grown free range (without a container). The color readings were taken outdoors under natural light. Color references are primarily to the R.H.S. Colour Chart of The Royal Horticultural Society of London.

GROWTH AND PROPAGATION

Plant type and use: Squamifoliate evergreen plant (conifer). It can be used solitarily in gardens or grouped as a field hedge.

Growth habit: Ovoid.

Height: 50 cm.

Spread: 22 cm.

Hardiness: Zone 5, between 28.8–23.4° C.

Propagation protocol: The new variety grafts well and, similar to 'Smaragd', 'Silvanus 1' can be propagated by cuttings successfully. As the plant takes root well, the cutting is the most important propagation protocol in the nursery. The cuttings are taken immediately from the semi-hardwood shoots taken off the mother plants. Please note that only semi-hardwood cuttings can root, as soft cuttings root off in the radication medium and cannot take root. Also, fewer cuttings can be taken from 'Silvanus 1' because it is slower growing than 'Smaragd'. The cuttings are taken from the end of August until April, by the beginning of prolification. The radication medium used is 0.2 mm granulation-sterile buddled gravel. For a better rooting, each cutting is dipped (about 1 mm deep) into 0.6% IBA (indole butric acid). The cuttings are grown in a temperate glasshouse. The temperature of the rooting medium should be between 19 and 20° C. and the temperature of the air must always be cooler. Low temperatures (up to −5° C.) also provide a stronger root system. Automatic overhead irrigation is supplied 2–3 times a day, depending on the weather. The cuttings take root in 9–12 weeks. The growing can then proceed in 9×9 plastic pots or in open ground.

Time to initiate roots: Approximately 42 to 56 days, with the temperature of radication medium being 19–20° C. and the maximum temperature of the air being 16–17° C.

Time to develop roots: Approximately 21 to 28 days, with the temperature of radication medium being 19–20° C. and the maximum temperature of the air being 16–17° C.

Rooting habit: Adventitious and fibrous root system.

Trunk:

*Surface texture.*—Reticulate and scaly.
*Color.*—Greyed-Orange group 177A.
*Diameter.*—28 mm at 50 mm in height.

Disease/pest resistance: No resistance or susceptibility has been observed to date.

STEM DESCRIPTION

Shape:

*Twigs.*—Upright.
*Mature branches.*—Upright.

Color:

*Twigs.*—Greyed-Orange Group 177B.
*Young branches.*—Greyed-Orange Group 164C.
*Mature branches.*—Greyed-Orange Group 177B.

Diameter:

*Twigs.*—8 mm.
*Main branches.*—5 mm.
*Secondary branches.*—2.5 mm.

Length (measured on a six-year old plant):

*Twigs.*—11.3 cm.
*Main branches.*—31.5 cm.
*Secondary branches.*—10.2 cm.

Surface description:

*Twigs.*—Fibrous, vertically striated.
*Main branches.*—Medium striation.
*Secondary branches.*—Minor striation.

Branching description: The branching is medium dense and it is arranged in vertical levels. The branching is similar to *Thuja orientalis* 'Aurea Nana' (syn: *Thuja orientalis* 'Berkmannii').

Branch aspect description: Similar to *Thuja occidentalis* 'Smaragd', but its structure is thinner and finer.

FOLIAGE DESCRIPTION

Leaf:

*Color.*—Green Group 143C.
*Arrangement.*—Opposite.
*Fragrance.*—Resin-smelling (if rubbed).
*Shape.*—Flattened squama.
*Length.*—2.5 mm.
*Width.*—Narrow, approximately 1.5–2 mm.
*Division.*—Overlap as a squama.
*Base.*—Oval.
*Apex.*—Pointed; sharp.
*Margin.*—Entire.
*Surface texture.*—Upper surface: Glandular points rise with an X motif because of overlapping scale leafs. Lower surface: X motif because of overlapping scale leafs.
*Resin glands.*—Location: At glandular point rises. Shape: Square. Color: Green.

Cone description: Not available as cones are not yet present.

Seed description: Not available as seeds are not yet present.

I claim:

1. A new and distinct variety of *Thuja occidentalis* plant named 'Silvanus 1' as is herein described and illustrated.

* * * * *